United States Patent [19]
Prendergast et al.

[11] Patent Number: 5,900,923
[45] Date of Patent: May 4, 1999

[54] PATIENT SIMULATOR EYE DILATION DEVICE

[75] Inventors: William K. Prendergast, Kirkwood, N.Y.; John T. Reed, Brackney, Pa.

[73] Assignee: MedSim-Eagle Simulation, Inc., Binghamton, N.Y.

[21] Appl. No.: 08/979,215

[22] Filed: Nov. 26, 1997

Related U.S. Application Data

[60] Provisional application No. 60/031,842, Nov. 26, 1996.

[51] Int. Cl.⁶ ........................................................ A61B 3/10
[52] U.S. Cl. ............................................. 351/221; 351/211
[58] Field of Search .................................... 351/221, 211, 351/212, 205, 246, 206, 247; 128/653.1, 644, 745

[56] References Cited

U.S. PATENT DOCUMENTS

| | | |
|---|---|---|
| 3,520,071 | 7/1970 | Abrahamson . |
| 5,114,222 | 5/1992 | Cornsweet .............................. 351/221 |
| 5,403,192 | 4/1995 | Kleinwaks . |

*Primary Examiner*—Hung Xuan Dang
*Attorney, Agent, or Firm*—Malin, Haley, DiMaggio & Crosby, PA

[57] ABSTRACT

A human eye dilation simulator is provided for use in a medical patient simulation mannequin. The eye simulator's pupils dilate and constrict in response to light stimuli, and physiological condition. Eyelids open, close, and blink under control of a simulation computer. The eyelids and can be opened manually for student examination, testing, and diagnosis. Each eye can be programmed independently with a variety of responses to simulate actual eye responses to various neurological dysfunction, trauma, or drugs. The eye simulator is used in conjunction with other responses from a patient simulator mannequin to simulate the bodily responses of an actual patient to various situations encountered in the medical field. The patient simulator is used for training medical personnel especially in the areas of trauma care and anesthesiology.

30 Claims, 7 Drawing Sheets

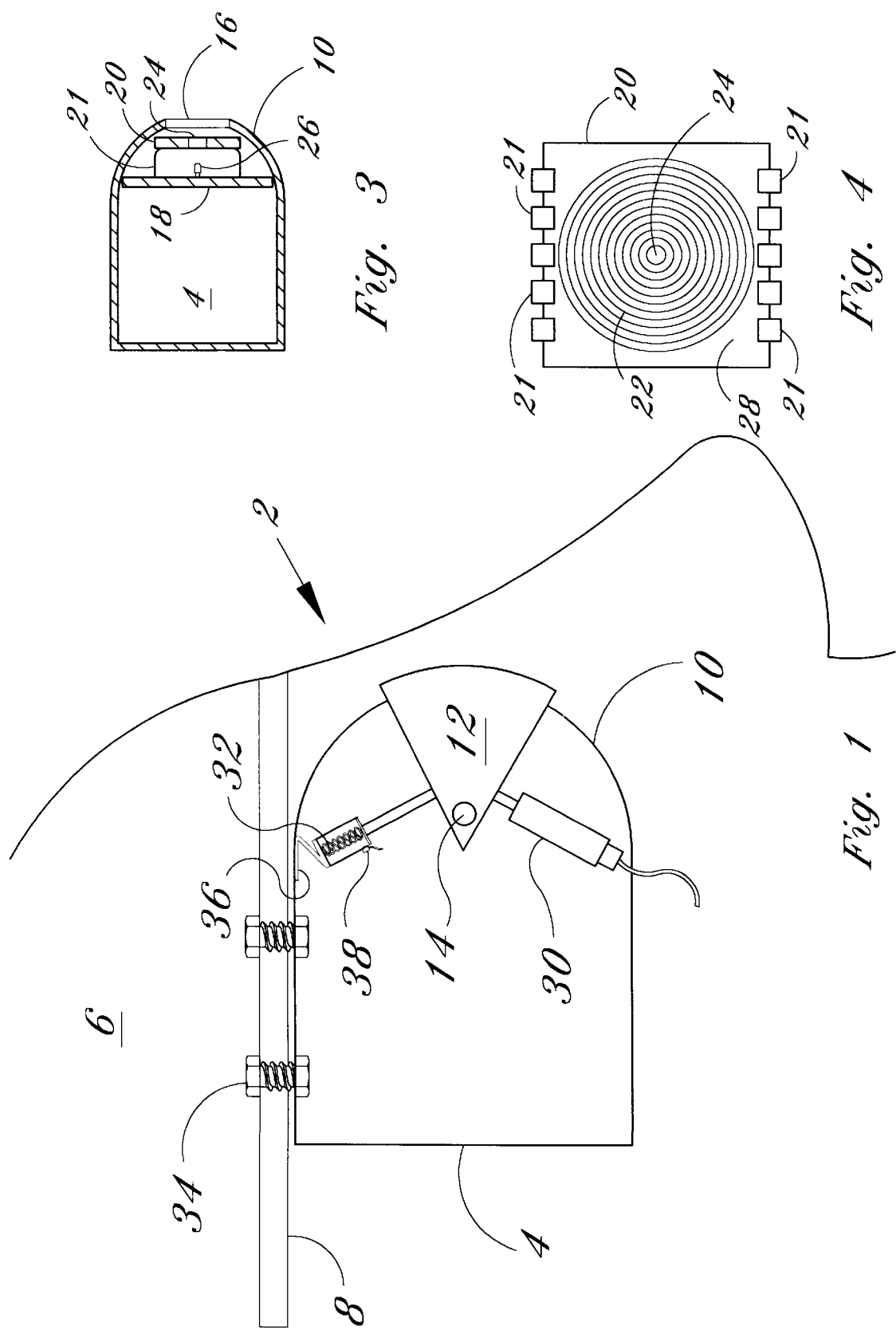

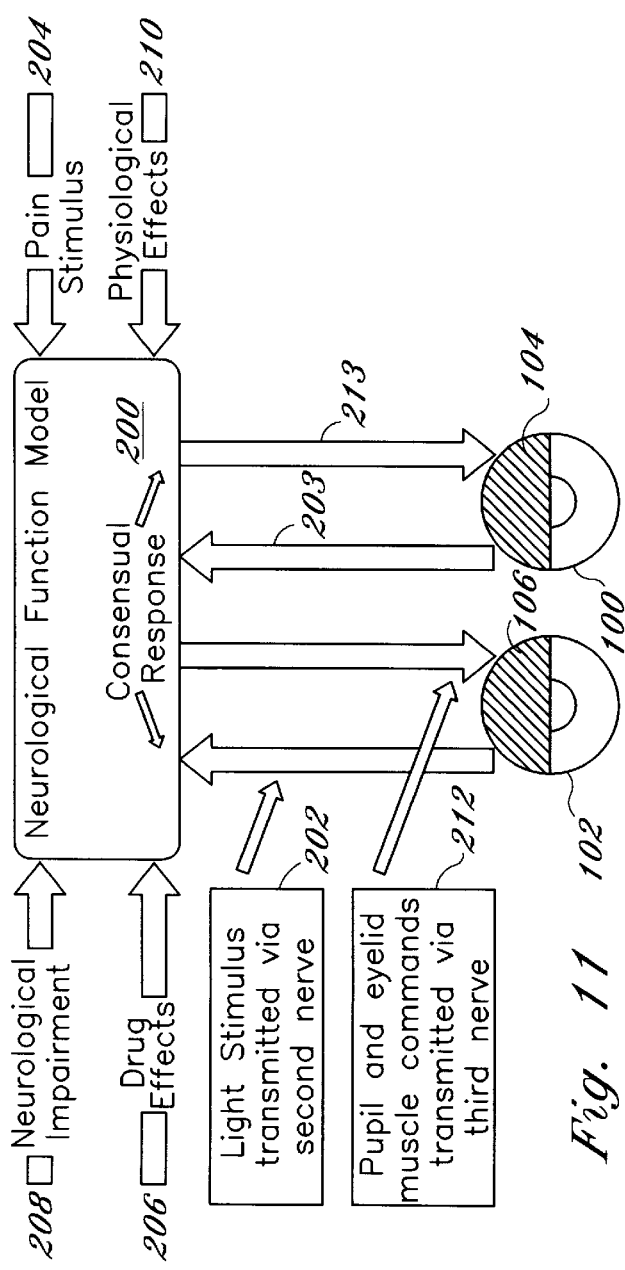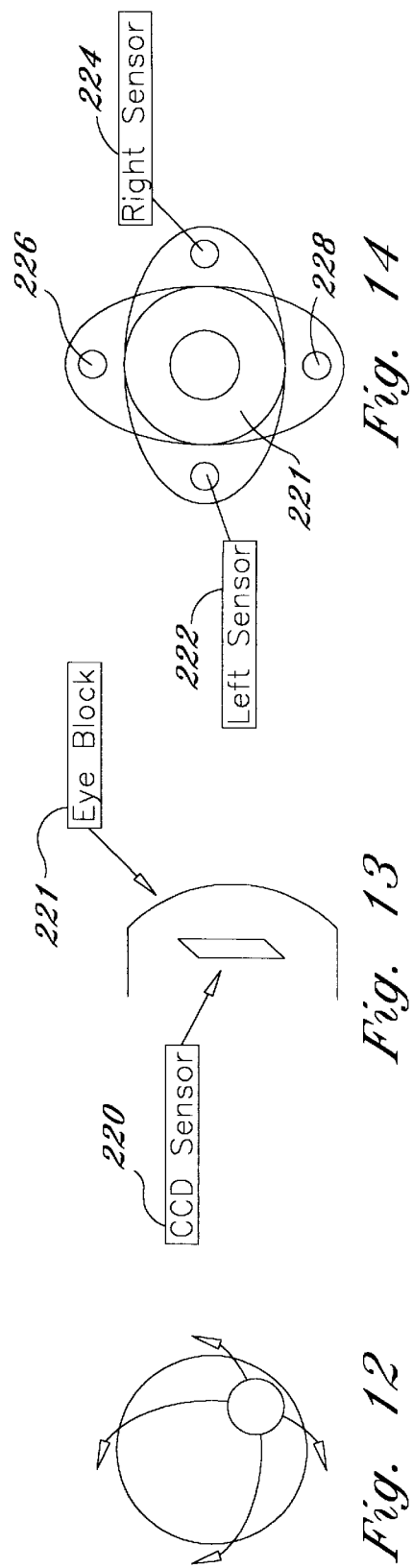
Fig. 11
Fig. 12
Fig. 13
Fig. 14

PATIENT SIMULATOR EYE DILATION DEVICE

CROSS-REFERENCE TO RELATED APPLICATIONS

This application claims the benefit of U.S. provisional application No. 60/031,842, filed Nov. 26, 1996.

BACKGROUND OF THE INVENTION

1. Field of the Invention

This invention relates to a patient simulator mannequin for use in training trauma medical personnel, physicians, and anesthesiologists, and more particularly to a realistic human eye simulator for a patient simulator mannequin that simulates pupil dilation and constriction responses to varying light levels, and eyelid control.

2. Description of Related Art

There are presently available patient simulator mannequins to train medical personnel in areas such as trauma treatment and anesthesiology. These mannequins typically have capabilities featuring spontaneous breathing and mechanical ventilation, thumb twitch, heart and breath sounds, pulses, and a complete airway anatomy for intubation and difficult airway training. Examples of anesthesiology simulator mannequins are disclosed in U.S. Pat. No. 5,403,192 to Kleinwaks et al., and in U.S. Pat. No. 3,520,071 to S. Abrahamson et al. (the '071 patent), the disclosures of which are incorporated herein by reference.

The traditional method of training in the medical profession involves proctoring where the student "learns by doing" at the elbow of an experienced person who guides and monitors the student's performance. This can put the patient at risk and limit the student's exposure to rare or critical events that do not occur very often. Using patient simulator mannequins, the student can develop skills in manual dexterity and diagnosis, recognize symptoms immediately, prescribe the right remedy, and correct the patient's condition, with none of the inherent risk.

Mannequins are particularly important for training in crisis management of critical events that happen rarely, especially in trauma and anesthesiology. The mannequins are typically computer controlled and be programmed for a variety of responses which simulate a variety of medical symptoms and problems. However, several human responses, such as independent eye pupil dilation and contraction, that are used to diagnose an actual patient's state, are lacking in the present simulators.

A bright light is used in trauma care to diagnose neurological injury or reaction to medication. In a patient with a properly functioning neurological system, the pupils should constrict when exposed to a bright light, and dilate again when the light stimulus is removed. In situations of neurological damage, or reaction to drugs and medication, the pupils of each eye may react differently to the same light stimuli.

Furthermore, a patient's state of consciousness is assessed by clues provided by the opening and closing of the patient's eyelids. Using present mannequins, which have no eye response, a complete patient exam, that would be conducted on an actual patient, is not possible.

Attempts have been made to provide simulator mannequins with eye response. For example, the '071 patent discloses a mannequin for use in anesthesiology training that provides limited eye response. The mannequin's eyelids open and close, and the simulated pupils dilate in a continuous change from normal to full dilation. Dilation of the pupils is provided by activation of a pneumatic actuator acting on a cam and cam follower to press a neoprene plunger into a plastic eye form. The harder the plunger is pressed by the actuator into the plastic eye form, the more the plunger's cone tip is flattened, thereby changing dilation diameters. However, there is no realistic eye response including no provision for individual control of the pupils and/or eyelids, or any response to a simulated patient state, or simulated patient physiology.

Hence, there exists the need for a realistic eye simulator to simulate human eye responses to a variety of stimuli, including normal and abnormal responses to a multitude of physiological conditions and drugs selected by the trainer. The eye simulator can be used, in combination with other simulated bodily responses, in patient simulator mannequins. Patient simulator mannequins, having a realistic eye simulator, can improve medical training realism using the mannequins because the responses of the mannequins would include eye responses that would normally be observed on an actual patient.

BRIEF SUMMARY OF THE INVENTION

The present invention simulates the reaction of a patient's eyes to a light stimulus based upon a preselected neurological and physiological condition of the patient. The eye simulator is controlled by a computer and has a simulated iris and pupil which dilates or constricts in response to varying levels of light, and in reaction to various medications given to the simulated patient and the patient's neurological condition. The eye simulator has artificial eyelids that can open, close, and blink under computer control, or be manually opened. The eye simulator responses are used in conjunction with and are coordinated with other artificial body responses in a patient simulator mannequin to simulate the occurrence of actual body responses to various medical situations and trauma.

The mannequin can simulate normal eye response functions or abnormal eye response functions, as selected and controlled by input from an operator or trainer to a control computer according to various trauma and physiological or neurological conditions, responses to drugs whether administered by the student or to simulate patient ingestion of drugs, and to respond according to emergency situations created by the trainer to simulate actual emergency conditions.

The eye simulator includes two simulated eyes each. Each eye in the eye simulator includes a thin, curved, opaque barrier shaped as an eyelid, an eyelid control motor, a large eye-shaped sphere having a liquid crystal display (LCD) embedded therein and positioned to represent the iris and pupil, and a light sensor or light sensitive receiver embedded near the LCD. LCD simulated eye functions are controlled by a computer and computer program electrically connected to the LCD, the light sensor, and the eyelid control motor or solenoid. The computer controls the LCD, which is comprised of concentric rings that under varying degrees of activation illuminate radially and concentrically to represent variations in pupil size in relation to light conditions received at the light sensor, and desired patient physiological reactions as input from the operator and/or physician trainer.

The simulator's physiological reactions are controlled by mathematical software models of human physiological reactions to various stimuli, drugs, and medical parameters. The software and control computer are under the control of the trainer who selects the desired parameters for the particular simulation exercise.

The eye simulator includes an enclosure or block, made of any suitable material, that functions as the simulated "eyeball" and is mounted inside the patient simulator mannequin's head on an internal mounting plate. The eye block is painted and rounded on the front portion to provide the shape and appearance of a natural looking human eye.

The simulated eyelid is a partially spherical, opaque cover of any suitable rigid material, sized to fit over the eye block. The eyelid is pivotally mounted and rotates from a fully down position, covering the eye, to a fully up position, retracted into the head, either manually or by solenoid or motor. The eyelid is biased by a spring mechanism to keep the eyelid in the closed position normally and can be driven into the open position by, for example, a solenoid or motor under computer control. Additionally, a student can manually open or close the mannequin's eyelids. A sensor, such as a microswitch, is used by the simulation computer to sense whether the eyelid is open or closed.

A circuit board is mounted in the eye block and used to electrically simulate and control the patient's liquid crystal display (LCD) iris and pupil. The LCD that forms changeable, visible light and dark concentric rings is electrically connected to the circuit board and is positioned, relative to the eye socket and eye ball housing, to simulate the iris and pupil of the artificial eye. When the eyelid is open, the front of the eye block has an optical or transparent window, or opening that allows the LCD display to be viewed.

The center of the LCD contains a small light-admitting cutout or aperture, or transparent window, that allows light to pass through the LCD display. A light-sensitive device, such as a phototransistor or photodiode, is mounted behind the LCD display to detect the presence of light that passes through the aperture/optical window in the center of the LCD display.

The LCD optically provides a reflective grey background in addition to the central optical window or aperture. Since the eye block is mounted enclosed in the mannequin skull of the patient simulator, the center aperture will appear black.

The LCD includes a plurality of concentric display rings, each one of which is individually connected to the display control circuit and is individually controlled. When a current is supplied to a display ring, the individual ring becomes opaque and appears black. By controlling each display ring from the center of the LCD radially outwardly, the apparent size of the center black area can be varied to represent visually the constricted or dilated pupil of a human eye. The non-black area surrounding the black area represents the iris. When the individual rings in the LCD are enabled electronically, they change from clear to black. The rings are activated and controlled by information from a computer program to the LCD control circuit starting from the ring near the center of the pupil and proceed radially concentrically outward depending on the simulated patient's current state and the applied stimulus including the brightness of the light contacting the light sensor.

In a human being, with the eyelid closed, a real pupil is dilated because there is little light applied to the eye. When open, a real eye is constricted by an amount that is dependent on, among other things, the amount of light applied to the eye. In the eye simulator, when the eyelid is closed, most of the inner rings will be enabled, simulating the pupil being large or dilated. When the simulated eyelid is open and light is applied, the phototransistor will detect the light and the simulation computer will cause the LCD to sequentially turn off several of the rings. The rings are deactivated sequentially from the outermost ring to the innermost ring. The pupil will appear to constrict as the outer rings being deactivated will display the grey LCD background as they change from black to clear.

When the light is removed, the process is reversed and, as the inner rings are activated, the pupil appears to dilate. By varying the speed and amount of constriction, and by independent reaction in each eye, various levels of patient neurologic dysfunction can be simulated. The mannequin's eyes will respond appropriately for different drugs that may be in the simulated patient or administered by the student. The student can learn how to use pupil dilation to assess the patient's condition. In addition, neurological trauma or dysfunction and/or drug reactions can cause individual pupils to react differently, and the eyelids to react abnormally, providing further assessment clues to the trainee.

The circuit and description are duplicated in each eye of the patient simulator and connected to the simulation computer. A computer program running on the simulation computer can control each eye individually to simulate dysfunction on the right or left side only. The simulation computer can blink the eyelids when the patient is conscious, or close the eyelids when unconscious. The student can manually open one or both eyelids to test either one or both pupil's reactions to light stimuli. The simulation computer program can program each eye to a react in a multitude of options such as constrict abnormally, exhibit no constriction, or be fully constricted or dilated to simulate various stages of neurological dysfunction and effects of various drugs, as selected by the trainer.

Accordingly it is an object of the present invention to provide a realistic artificial eye for use in a medical patient simulator.

It is a further object of the present invention to provide a human eye simulator with a realistic iris and pupil image that can constrict or dilate in response to light stimuli, normal and abnormal physiological functioning, and/or drug reactions, and the conscious or unconscious state of the simulated patient.

It is still a further object of the present invention to provide an eye simulator that has an eyelid that opens, closes, and blinks.

It is yet a further object of the present invention to provide an eye simulator that permits manual opening of the eyelid and detection of the eyelid position by a computer controller.

It is yet a further object of the present invention to provide an eye simulator where each eye is individually controlled.

It is still a further object of the present invention to provide an eye simulator that is computer controlled and is easily programmable to respond in a multiplicity of ways to light stimuli and normal and abnormal neurological functioning, and drug reaction.

In accordance with these and other objects which will become apparent hereinafter, the instant invention will now be described with particular reference to the accompanying drawings.

BRIEF DESCRIPTION OF THE SEVERAL VIEWS OF THE DRAWINGS

FIG. 1 is a side elevational view of the present invention showing the eyelid closed.

FIG. 3 is a side elevational view in cross-section showing the inside of the eye block.

FIG. 4 is a front elevational view of the liquid crystal display of the present invention.

FIG. 11 is a diagrammatic view of one embodiment of the neurological function model of the present invention.

FIG. 12 is a diagrammatic view of a gimbaled eyeball for an alternate embodiment of the present invention.

FIG. 13 is a diagrammatic view of a light sensor for use in the embodiment of FIG. 12.

FIG. 14 is a front elevational view of an alternate embodiment of that in FIG. 13.

DETAILED DESCRIPTION OF THE INVENTION

Figure 2:
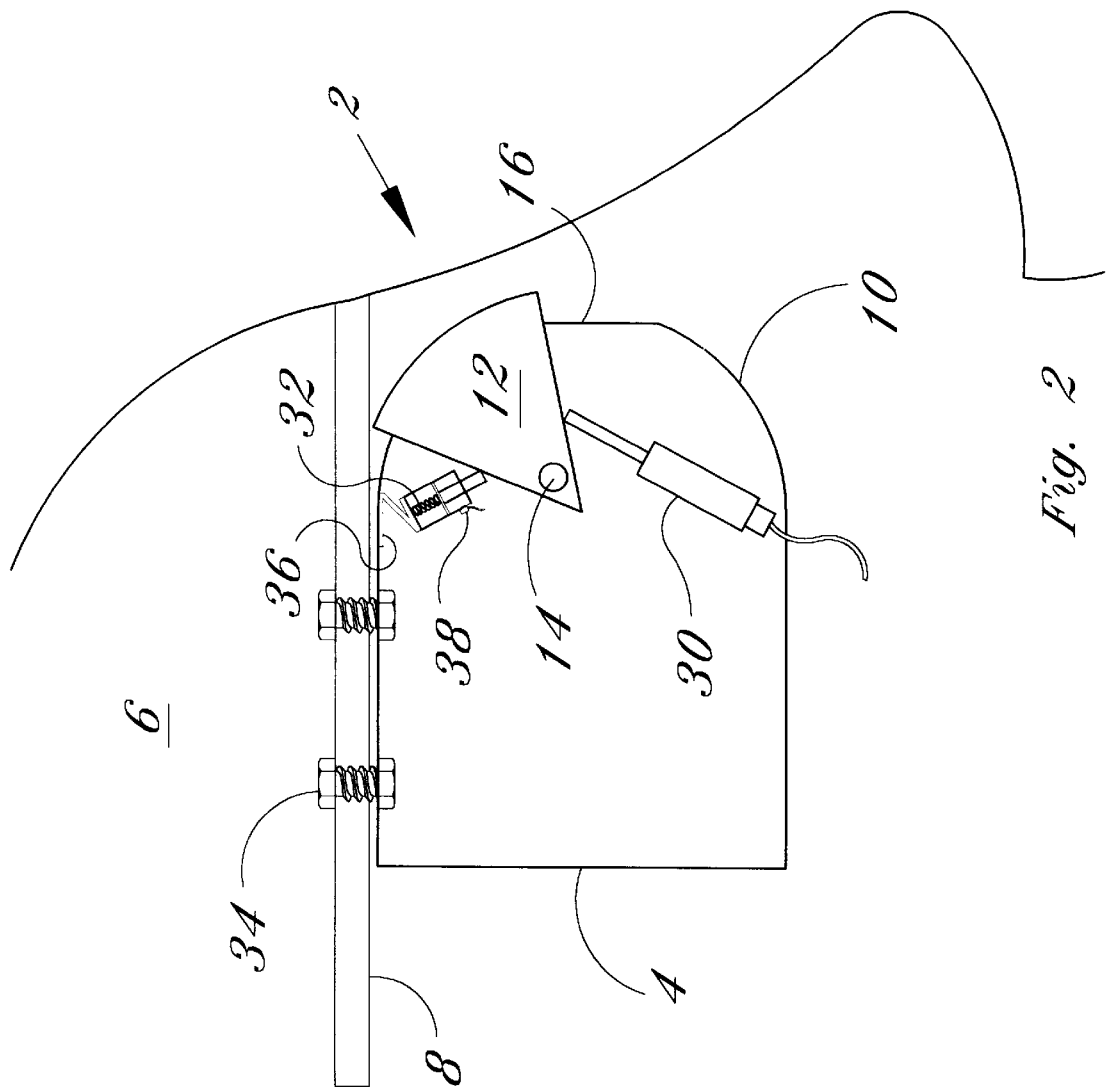
FIG. 2 is a side elevational view of the present invention showing the eyelid open.

Referring now to the drawings, and in particular to FIGS. 1 and 2, eye simulator 2 of the present invention includes an enclosure or block 4, made of any suitable material including, but not limited to, plastic, metal, glass, or wood, that functions as the "eyeball" and is mounted inside the patient simulator mannequin's head or skull 6 in any suitable manner. One example of a mounting structure can include internal mounting plate 8 and a suitable fastener, such as screws or bolts 34. Eye block 4 is painted and rounded on front portion 10 to form the shape and appearance of a natural looking artificial eye.

Figure 7:
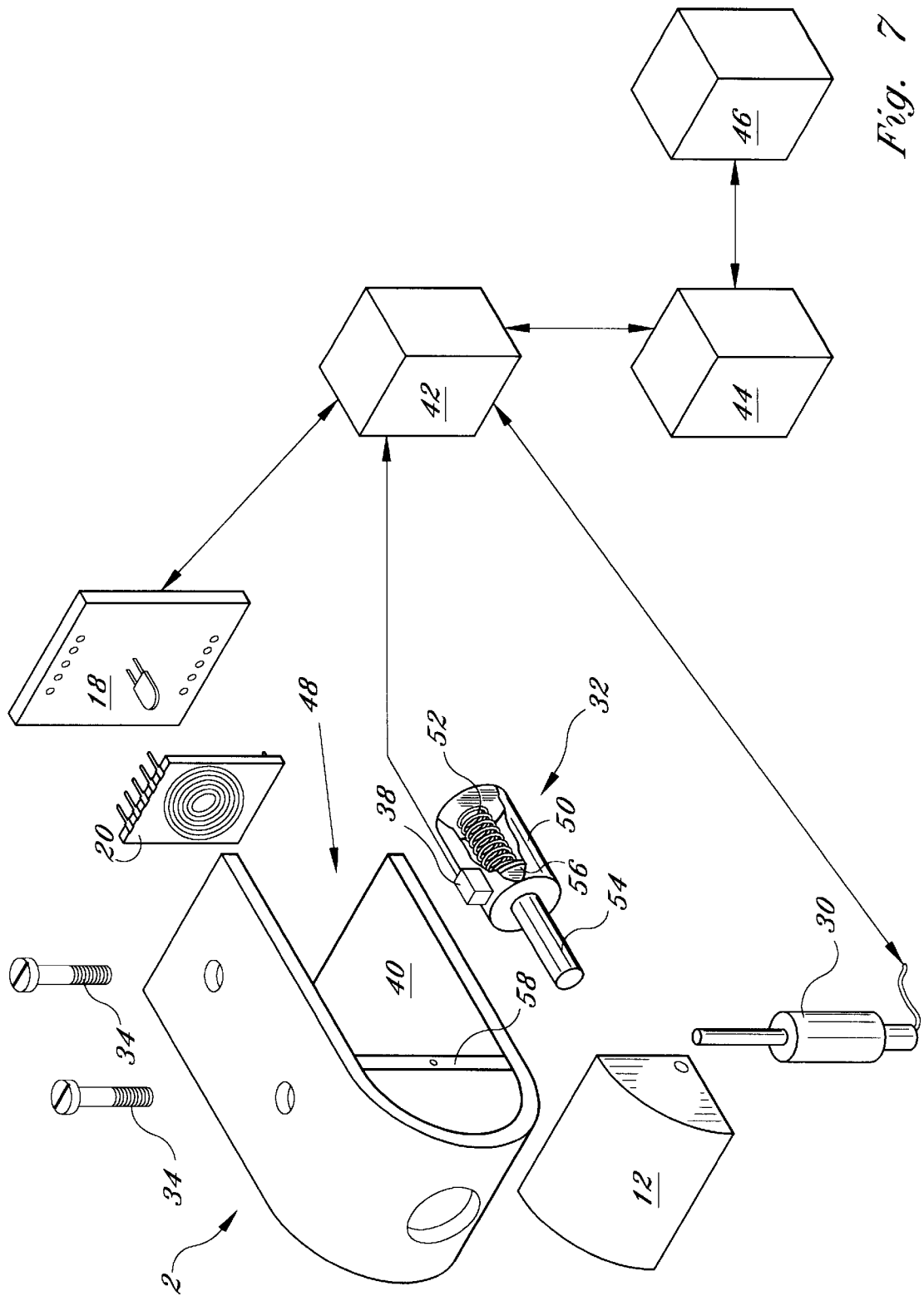
FIG. 7 is an exploded diagrammatic view of the present invention.

Alternate shapes and constructions of eye blocks can be utilized and made to appear as a human eye when viewed from the front, as further described herein below. For example, as shown in FIG. 7, an eye block 40 may include open sides 48. Other shapes and constructions of eye blocks are considered within the scope of the invention.

Eyelid 12 is a rounded cover, of any suitable material including plastic, vinyl, metal or other material, made to appear skin-like and sized to fit over rounded portion 10 of eye block 4. Eyelid 12 rotates about pins 14 (one on each side with only one shown in the Figs.) to rotate from a fully down position, covering the eye pupil as shown in FIG. 1, to a fully up position, exposing the eye pupil through aperture 16 (described below) in eye block 4, as shown in FIG. 2. Eyelid 12 is preferably biased in the closed position by a suitable mechanism, such as spring 32, and can be driven into the open position by suitable means, such as conventional solenoid 30, under control of the simulation computer 42, shown in FIG. 7. Preferably eyelid 12 will be biased in the closed position and driven into the open position by the computer as shown, but could alternately be biased into the open position and driven closed (not shown). The eyelids 12 can also be manually opened such as by a student during an exam of the simulated patient.

Alternately, as shown in FIG. 7, eyelid 12 can be attached to eye block 40 with open sides 48 by suitable support members such as 58, one member 58 being on each side of eye block 40 (only one member 58 shown). Other shaped eye blocks may require variations on attachment of eyelid 12, as further described hereinbelow, and, which are considered within the scope of the invention.

A standard sensing device, such as microswitch 38, is used by the simulation computer 42 to sense whether eyelid 12 is open or closed. Microswitch 38 can be located in any suitable location, such as attached to spring mechanism 32, as shown in FIGS. 1, 2, and 7. Spring mechanism 32 can be made of housing 50, internal spring 52, plunger 54, and internal base plate 56. Internal spring 52 presses against base plate 56 which is attached to plunger 54. Spring mechanism 32 can be attached to eye block 4 by using bracket 36 to position spring 32 such that plunger 54 impinges eyelid 12 to bias eyelid 12 into the closed position covering opening 16. Bracket 36 can be attached to eye block 4 by any suitable fastener including one of bolts 34 (not shown).

Referring now to FIGS. 3 and 4, a conventional electrical circuit (not shown) is mounted on circuit board 18 which is mounted in eye block 4 and used, under computer control 42, to control the liquid crystal display (LCD) 20 for simulation of a patient's pupil. Liquid crystal display (LCD) 20 forms concentric rings 22 and is mounted to circuit board 18 and electrically connected via a suitable manner such as a plurality of contacts 21. LCD display 20 is positioned in eye block 4 to form the iris and pupil of the artificial eye.

The front of eye block 4 has an optical or transparent window, such as aperture 16 that is sized to allow a suitable portion of LCD display 20 to be viewed.

The center of the LCD display 20 contains a small optical or transparent window such as aperture 24 that allows light to pass through LCD display 20. A suitable light sensitive device, such as phototransistor 26, is mounted behind LCD display 20 on circuit board 18 to detect the presence of light that passes through aperture 24 in the center of LCD display 20.

LCD display 20 has a reflective grey background 28, and aperture 24 in the center. Since eye block 4 is mounted enclosed in skull 6 of a patient simulator which is essentially void of light internally, the center aperture 24 will appear black. Similar to an LCD wrist watch display, LCD concentric rings 22 are clear when deactivated and appear black when activated. When deactivated, concentric rings 22 are clear and thus allow grey background 28 of display 20 to be visible. When the individual LCD concentric rings 22 in LCD display 20 are enabled electronically, their appearance changes from clear to black.

Figure 5:
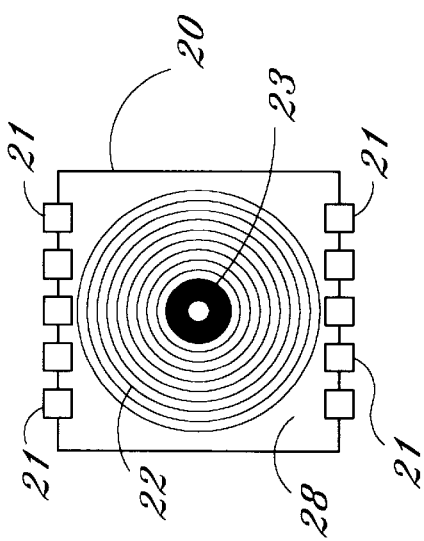
FIG. 5 is a front elevational view of the liquid crystal display of the present invention shown dilated.
Figure 6:
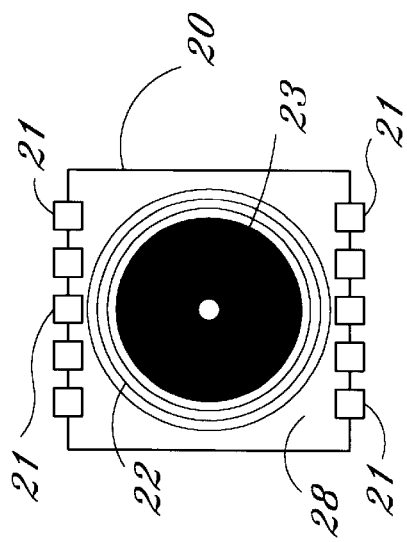
FIG. 6 is a front elevational view of the liquid crystal display of the present invention shown constricted.

Referring now to FIGS. 5 and 6, concentric rings 22 are activated starting from the ring near the center of the iris closest to the pupil and proceed sequentially radially concentrically outward, and are deactivated starting at the outermost ring and proceed sequentially radially concentrically inward. The number of activated rings 23 is dependent upon and proportional to the brightness of the light contacting phototransistor 26, and according to computer control 42 as input from trainer control 44 to simulate various physiological conditions.

In a real patient with normal function, when the eyelid is closed, the pupil is dilated because there is little light applied to the eye. When open, a real eye's pupil is constricted by an amount that is dependent upon and proportional to, among other physiological factors, the amount of light applied to the eye.

In eye simulator 2, when eyelid 12 is closed, most of the inner rings of LCD concentric rings 22 will be enabled 23 and black, simulating the pupil being large or dilated, as shown in FIG. 5. When eyelid 12 is open and light is applied, phototransistor 26 will detect the light through aperture 24, and the simulation computer 42 and computer program will cause LCD display 20 to sequentially turn off or deactivate several of the outermost activated rings 23 of LCD display 20, thereby reducing the number of activated rings 23, as shown in FIG. 6. LCD display 20 will appear as a pupil that is constricting as the rings of LCD concentric rings 22 are deactivated displaying grey LCD background 28 as rings 22 change from black to clear.

When the light is removed, the process is reversed and, as the inner rings of LCD concentric rings 22 are activated and change from clear to black, the artificial eye appears to dilate. By using simulation computer 42, and computer program 44 controlled by trainer 46, as shown in FIG. 7, to vary the speed and amount of concentric ring activation and deactivation, or constriction, normal and abnormal eye responses, including responses to various levels of patient neurologic dysfunction and responses to various drugs, can be simulated. Using a patient simulator mannequin with eye response, the student can learn how to use pupil dilation to assess the patient's condition.

Referring now to FIG. 7, the computer program 44, that controls computer 42, includes mathematical software models of human physiological reaction to various stimuli, such as light reaching the eye and drug reaction, and various levels of neurological functioning ranging from normal to abnormal, whether caused by trauma, drugs, or diseases. The parameters needed by the mathematical models used in computer program 44 are controlled by input from the physician trainer 46. The physician trainer 46 can thus input any of a multitude of training scenarios for the student trainee.

The above description is given for one eye simulator 2 but is duplicated in each eye of the patient simulator and connected to the simulation computer 42. The simulation computer program 44, upon input from trainer 46, controls each eye individually to simulate dysfunction on the right or left side only. The simulation computer 42 can blink eyelids 12 when the patient is conscious, or close the eyelids when unconscious. The student can manually open one or both eyelids to test either one or both pupils to light stimuli. The simulation computer 42 can program each eye to react in a multitude of responses such as constrict abnormally, exhibit no constriction, or be fully constricted or dilated to simulate various stages of neurological dysfunction, or the correct response to various drugs that may be in the patient, all at the direction of computer program 44 and input from trainer 46.

Figure 8:
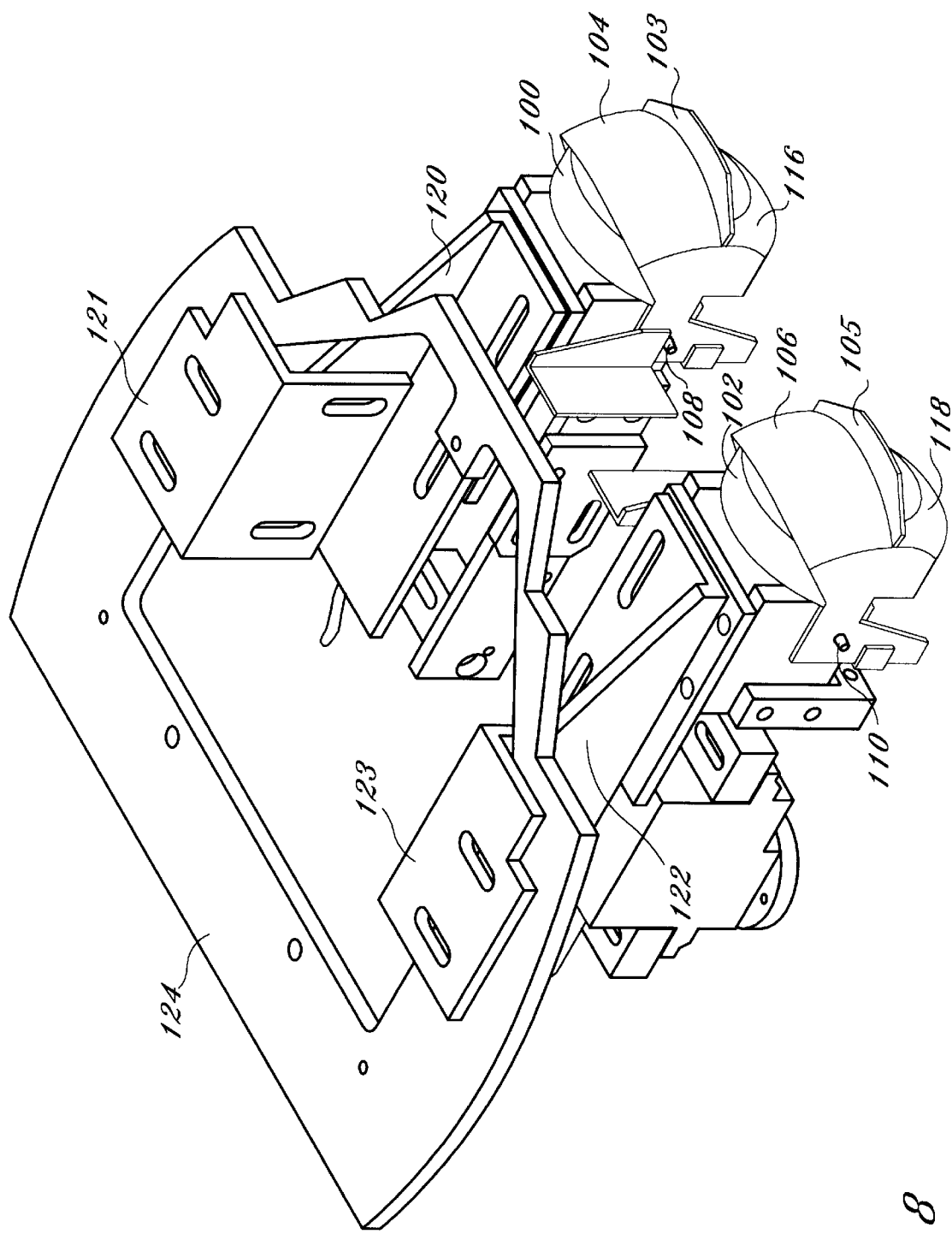
FIG. 8 is a front perspective view of the preferred embodiment of the present invention illustrated with the eyelids closed.
Figure 9:
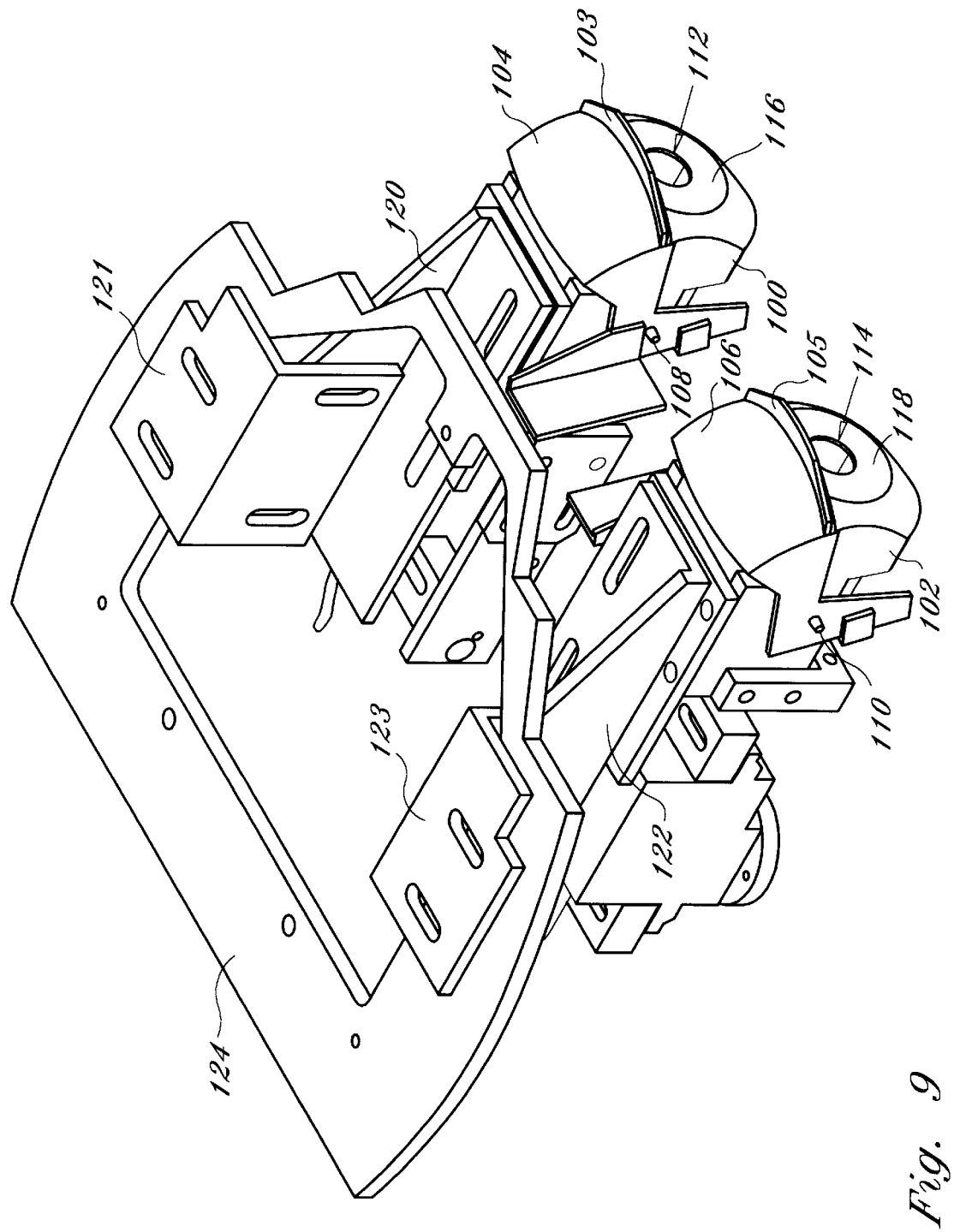
FIG. 9 is a front perspective view of that of FIG. 8 illustrated with the eyelids open.

Referring to FIG. 8, a preferred embodiment of the present invention is illustrated, and includes both a left and right simulated eye. Simulated eyeballs 100 and 102 are covered by simulated eyelids 104 and 106, which can have simulated eyelashes 103 and 105. Referring also to FIG. 9, eyelids 104 and 106 pivot about shafts 108 and 110, respectively. In the open position, simulated eyelids 104 and 106 expose apertures 112 and 114, respectively. The front portions 116 and 118, respectively, of simulated eyeballs 100 and 102, are shaped and made to appear similar to the front of a real eye. Behind apertures 112 and 114 are mounted displays 20, as described herein above.

Simulated eyeballs 100 and 102 can be attached by suitable brackets 120 and 122 to mounting plate 124, and can include other mounting brackets such as 121 and 123.

Figure 10:
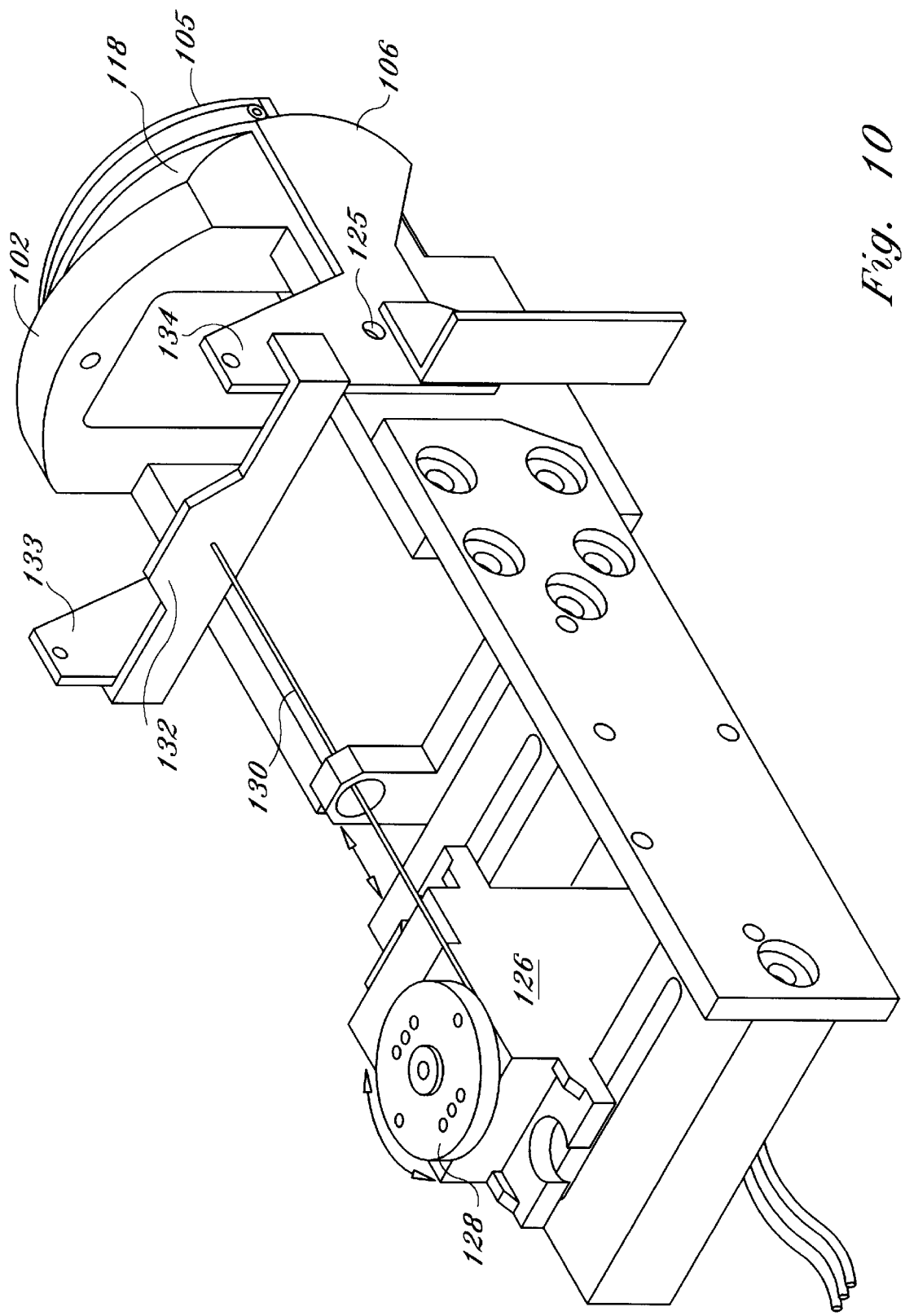
FIG. 10 is a bottom perspective view of a portion of that illustrated in FIG. 8.

Referring to FIG. 10, simulated eyeball 102 is illustrated upside down to show one embodiment of associated linkage as described herein. Eyeball 100 is not separately illustrated as it is a mirror image of eyeball 102.

Eyelid 106 rotates about shaft 110 at apertures 125 (as shown in FIGS. 8 and 9), to open and close eyelid 106 over the front portion 118 of eyeball 102, thereby selectively exposing or covering aperture 114. (Only one aperture 125 is visible in FIG. 10). Rotation of eyelid 106 can be accomplished manually by the user, or under computer control.

A motor or solenoid 126, under computer control, rotates plate 128 to linearly move linkage bar 130. Linkage bar 130 is attached to bracket 132. Bracket 132 is attached to eyelid 106 at flanges 133 and 134. Thus, rotational movement of plate 128 is translated to linear movement in bar 130, bracket 132, and flanges 133 and 134. The offset mounting position of bracket 132 on flanges 133 and 134, in relation to apertures 125, creates a fulcrum at apertures 125. Hence, the linear movement of flanges 133 and 134 causes eyelid 106 to rotate about shaft 110 at apertures 125, and to selectively cover and uncover the front portion 118 of eyeball 102, and thereby covering and uncovering aperture 114. Behind aperture 114 can be mounted display 20, as described herein above, and not specifically illustrated in FIGS. 8–10.

And yet another alternate embodiment of this invention would be a mechanical shutter that opens and closes electromechanically that replaces the liquid crystal display. The mechanical shutter would be a plurality of thin, sliding plates, much like a camera shutter, that together form a closed position that could be disposed about an artificial iris having a large aperture representing an enlarged pupil, with the mechanical shutter having a colored surface the same color as the iris in a closed position, which allows it to open, exposing a black surface beneath that represents the pupil. The plates could be spring-loaded in a closed or open position and electrical motors could be connected to the plates to pull them in a pivotal or slidable direction to create what appears to be a roughly circular aperture that is variable in radius, representing the iris contraction and pupil opening.

It is another embodiment of the invention that the iris/ pupil display can be represented by an elastic membrane or diaphragm that has a central aperture that could be electromechanically opened and closed by radial connectors that pull away from the membrane center to enlarge the circular opening through the use of electrical motors. For example, a latex member having a small opening cut through it could be pulled radially in several directions at the same time by one or more electrical motors, exposing a roughly circular opening, behind which could be a black surface representing the pupil. The latex or elastic material could be painted the color of the iris and disposed in the location of the iris beneath a simulated eyeball to provide the effect of an opening and closing pupil by contraction of the iris. Again, the electrical motors would be controlled by computer so that the activities of the iris and pupil would be in conjunction with the particular medical problems that are driven by the computer program.

Referring to FIG. 11, neurological function model 200 (used to control the simulation computer together with input from the instructor) is essentially a software model of human physiological reaction to various stimuli, such as light reaching the eye and drug reaction, and various levels of neurological functioning ranging from normal to abnormal, whether caused by trauma, drugs, or diseases.

The simulated eye's responses to the various inputs can be determined by the neurological function model 200. Alternately, the responses can be predetermined by the instructor, or by a combination of the instructor and the model.

The overall function of neurological model 200 includes input from the light sensors, discussed herein above, of the amount of light applied in each eye (100 and 102). The light stimulus data is presented to "brain" model 200 via simulated second cranial nerves 202 and 203. If the second cranial nerve is impaired for an eye (202 or 203), the light stimulus from that eye is ignored. The instructor controls the second cranial nerve state for each eye.

The light stimulus from each eye that reaches the brain model 200 are combined to simulate consensual response, which for a bright light applied to either eye causes constriction of both eyes.

Model 200 combines light stimulus and pain stimulus 204 to form a desired pupil reaction. Pain stimulus 204 can also be used to open the eyelids 104 and 106 depending on the state of the patient.

Pupil (constriction and dilation, and eyelid responses are further affected by drugs 206, neurological impairment 208, and physiological effects 210 including blood pressure, hypoxia, and the like.

In the absence of abnormal events, normal eyelid motion such as closing when the simulated patient falls asleep, or blinking spontaneously when awake can be simulated. The simulated eyelid response is affected by drug input 206, neurological impairment 208, and physiological effects 210. Other eyelid responses, such as eyelid flutter during seizures, can also be simulated.

The computed responses from model 200, based upon all the model's inputs, for the pupils and the eyelids are transmitted back to the eyes (100 and 102) and eyelids (104 and 106) via simulation of the third cranial nerves 212 and 213. If the third cranial nerve (212 or 213) is damaged for an eye, the muscle commands transmitted back to the eye and eyelid are ignored. The instructor controls the state of the third cranial nerve (212 and 213) for each eye.

Pupil constriction or dilation commands and/or eyelid motion commands are transmitted via the third cranial nerve (212 or 213) and are used to change the size of the pupil, and/or to change the position of the eyelid.

The pupil and eyelid responses are affected by simulated neuro-muscular blockade (NMB) drugs (206) that can prevent the "muscles" of the pupil or eyelid from responding to their associated commands.

Eye tracking that is performed during neurological assessment can also be simulated. Referring to FIG. 12, the simulated eye of the present invention can be mounted to a two-way gimbal to provide rotational movement of the simulated eyeball. The eyeball can then track, or rotate in the direction of the applied light.

Referring to FIG. 13, the light sensor mounted behind the simulated pupil of the eye block 221 can be replaced with a more elaborate sensor 220, such as a CCD camera chip, that can sense position as well as light level.

Alternately, as illustrated in FIG. 14, additional light sensors could be positioned left 222, right 224, above 226, and below 228, the simulated eye 221.

The light image on the sensor 220 or the differential light sensed by the individual sensors (222, 224, 226, and 228) allow the computer to determine the direction of the source of applied light. Appropriate "muscle" commands are sent via simulated nerve pathways resulting in motor commands to move the individual eyeball mechanisms right, left, up, and down, accordingly.

Motions of the simulated eye can be used to determine simulated neurological dysfunction, seizures, REM sleep, and other simulated conditions to be assessed by a trainee. As defined in the pupil and eyelid function description herein above, drugs, impairment, and physiological parameters would also effect eye tracking functions.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A patient simulator eye dilation apparatus comprising:
   a housing having an essentially hemispherical end, said housing having an opening centrally located in said hemispherical end;
   means for display, said means for display mounted inside said housing and adjacent said opening, said means for display including a centrally located hole and a plurality of concentric display sections;
   means for sensing light, said means for sensing light mounted inside said housing and adjacent said hole;
   means for activating said means for display, said means for activating sensitive to said means for sensing light, said means for activating including control means for selectively controlling said plurality of concentric display sections.

2. The apparatus as claimed in claim 1 further comprising:
   means for covering said opening, said means for covering movably related to said housing, said means for covering sized and shaped to closely fit over said hemispherical end, said means for covering movable from a first position covering said opening to a second position uncovering said opening.

3. The apparatus as claimed in claim 2 further including means for moving said means for covering between said first position and said second position.

4. The apparatus as claimed in claim 1 wherein said means for display is a liquid crystal display having a plurality of liquid crystal concentric sections.

5. The apparatus as claimed in claim 1 wherein said means for activating includes a programmable computer and computer program, said means for controlling responsive to a preselected simulated physiological state for the patient simulator.

6. The apparatus as claimed in claim 5 wherein said means for covering is biased in said first position or said second position.

7. The apparatus as claimed in claim 1 wherein said means for sensing light is a photodiode or phototransistor.

8. A patient simulator eye dilation apparatus comprising:
   an opaque housing having an essentially hemispherical end, said housing having a transparent portion centrally located in said hemispherical end;
   means for display, said means for display mounted inside said housing and adjacent said transparent portion, said means for display including a centrally located transparent window and a plurality of concentric display sections;
   means for sensing light, said means for sensing light mounted inside said housing and adjacent said transparent window;
   means for activating said means for display, said means for activating sensitive to said means for sensing light, said means for activating including control means for selectively controlling said plurality of concentric display sections.

9. The apparatus as claimed in claim 8 further comprising:

opaque means for covering said transparent portion, said opaque means for covering movably connected to said housing, said opaque means for covering sized and shaped to closely fit over said hemispherical end, said opaque means for covering movable from a first position covering said transparent portion to a second position uncovering said transparent portion.

10. The apparatus as claimed in claim 9 further including means for moving said opaque means for covering between said first position and said second position.

11. The apparatus as claimed in claim 10 wherein said opaque means for covering is biased in said first position or said second position.

12. The apparatus as claimed in claim 8 wherein said means for display is a liquid crystal display having a plurality of liquid crystal concentric sections.

13. The apparatus as claimed in claim 8 wherein said means for activating includes a programmable computer and computer program, said means for controlling responsive to a preselected simulated physiological state for the patient simulator.

14. The apparatus as claimed in claim 8 wherein said means for sensing light is a photodiode or phototransistor.

15. A patient simulator eye dilation apparatus comprising:

a display having a centrally located hole and a plurality of concentric display sections;

means for sensing light mounted adjacent said hole;

means for activating said display, said means for activating sensitive to said means for sensing light, said means for activating including control means for selectively controlling said plurality of concentric display sections.

16. The apparatus as claimed in claim 15 further comprising:

a housing having an essentially hemispherical end, said housing having an opening centrally located in said hemispherical end, said display mounted inside said housing adjacent said opening, said means for sensing light mounted in said housing.

17. The apparatus as claimed in claim 16 further comprising:

an opaque barrier for said opening movably connected to said housing, said opaque barrier sized and shaped to closely fit over said hemispherical end, said opaque barrier including means for moving between a first position covering said opening and a second position uncovering said opening.

18. The apparatus as claimed in claim 17 wherein said opaque barrier is biased in said first position or said second position.

19. The apparatus as claimed in claim 15 wherein said display is a liquid crystal display having a plurality of liquid crystal concentric sections.

20. The apparatus as claimed in claim 15 wherein means for activating includes a programmable computer and computer program, said means for controlling responsive to a preselected simulated physiological state for the patient simulator.

21. The apparatus as claimed in claim 15 wherein said means for sensing light is a photodiode or phototransistor.

22. An apparatus for simulating human eye dilation for use in a patient simulator mannequin comprising:

means for visually representing a pupil and iris of a human eye;

means connected to said means for visually representing a pupil and iris of a human eye for changing the visually perceived diameter of said pupil to simulate dilation of said pupil; and means for control connected to said means for changing the visually perceived diameter of said pupil, said means for control responsive to varying levels of applied light stimulus and a preselected simulated physiological state of said patient simulator mannequin.

23. A simulated human eye for use in medical training to provide realistic human-like variable responses of constriction of the iris and pupil to different light sources and to simulated medical problems that evidence an appropriate simulated medical condition comprising:

a surface connected to said housing for simulating an eyeball;

a visual display disposed in a proximate relationship to said surface, said display including a representation visually of the human iris and pupil; and a display controller connected to said display for changing visually the size of said simulated iris to enlarge or diminish the pupil image simulator dilation and contraction.

24. A simulated human eye as in claim 23, including:

a light-sensitive device connected to said display controller and mounted proximate to said visual display for changing, the size of said simulated iris being varied whenever light is received by said light-sensitive means.

25. A simulated human eye as in claim 23, wherein said simulated eye is mounted in a mannequin.

26. A simulated human eye as in claim 23, including:

a computer and computer software program connected to said display controller for providing simulated computer driven health problems that relate to the size of the pupil in a human being for providing realistic medical training, wherein the simulated human eye provides dilation and contractions relative to a plurality of different health problems in the computer program.

27. The simulated human eye as in claim 26, wherein said eye includes means for rotational movement for said eye to realistically track a moving source of light input.

28. The simulated human eye as in claim 23, wherein said display controller is controlled by a simulated physiological state preselected by an operator.

29. The simulated human eye as in claim 23, wherein said computer software program includes a neurological function model including inputs for neurological impairment, drug effects, pain stimulus, and physiological effects, and outputs for controlling pupil constriction and eyelid movement.

30. The simulated human eye as in claim 29, wherein there are two simulated eyes and said neurological function model provides independent control signals for controlling pupil constriction and eyelid movement in each simulated eye.

* * * * *